United States Patent [19]

Berg

[11] Patent Number: 5,470,443
[45] Date of Patent: Nov. 28, 1995

[54] SEPARATION OF ISOPROPANOL FROM 2-BUTANONE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 370,624

[22] Filed: Jan. 10, 1995

[51] Int. Cl.$^6$ ............ B01D 3/40; C07C 31/10; C07C 45/83
[52] U.S. Cl. ............ 203/57; 203/58; 203/59; 203/60; 203/62; 203/63; 203/64; 203/65; 568/410; 568/913
[58] Field of Search ............ 203/65, 59, 57, 203/60, 63, 62, 58, 64, 52; 568/410, 913, 918

[56] References Cited

U.S. PATENT DOCUMENTS

| | | | |
|---|---|---|---|
| 2,552,412 | 5/1951 | Drout et al. | 203/84 |
| 2,559,519 | 7/1951 | Smith et al. | 203/84 |
| 2,570,205 | 10/1951 | Carlson et al. | 203/84 |
| 2,575,285 | 11/1951 | Carlson et al. | 203/85 |
| 2,583,412 | 1/1952 | Carlson et al. | 203/65 |
| 2,591,712 | 4/1952 | Morrell et al. | 203/52 |
| 2,591,713 | 4/1952 | Morrell et al. | 203/52 |
| 2,617,757 | 11/1952 | Michael | 203/52 |

*Primary Examiner*—Wilbur Bascomb, Jr.

[57] ABSTRACT

Isopropanol is difficult to separate from 2-butanone by conventional distillation or rectification because of the proximity of their boiling points. Isopropanol can be readily separated from 2-butanone by extractive distillation. Effective agents are o-cresol, ethylene glycol and nitroethane.

2 Claims, No Drawings

SEPARATION OF ISOPROPANOL FROM 2-BUTANONE BY EXTRACTIVE DISTILLATION

FIELD OF THE INVENTION

This invention relates to a method for separating isopropanol from 2-butanone using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect Of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes that produce complex mixtures of oxygenated compounds, e.g. the Fischer-Tropsch process. Two of the commonest oxygenated compounds usually present are 2-butanone, B.P=80° C. and isopropanol, B.P.=82° C. The relative volatility between these two is 1.35 which makes it difficult to separate them by conventional rectification. Extractive-distillation would be an attractive method of effecting the separation of 2-butanone from isopropanol if agents can be found the (1) will create a large apparent relative volatility between 2-butanone and isopropanol and (2) are easy to recover from the 2-butanone. Table 2 shows the relative volatility required to obtain 99% purity. With no agent, 42 actual plates are required. With an agent giving a relative volatility of 2.3, only 15 actual plates are required.

TABLE 2

Theoretical and Actual Plates Required vs. Relative Volatility for 2-Butanone - Isopromanol Separation

| Relative Volatility | Theoretical Plates Required At Total Reflux, 99% Purity | Actual Plates Required 75% Efficiency |
|---|---|---|
| 1.35 | 31 | 42 |
| 1.7 | 17 | 23 |
| 2.3 | 11 | 15 |

OBJECTIVE OF THE INVENTION

The object of this invention is to provide a process or method of extractive distillation that will enhance the relative volatility of 2-butanone from isopropanol in their separation in a rectification column. It is a further object of this invention to identify organic compounds which in addition to the above constraints, are stable, can be ,separated from 2-butanone and recycled to the extractive column with little decomposition.

SUMMARY OF THE INVENTION

The objects of this invention are to provide a process for separating 2-butanone from isopropanol which entails the use of certain organic compounds as the agent in extractive distillation.

DETAILED DESCRIPTION OF THE INVENTION

I have discovered that certain organic compounds will greatly improve the relative volatility of isopropanol from 2-butanone and permit the separation of isopropanol from 2-butanone by, rectification when employed as the agent in extractive distillation. Table 3 lists the compounds that I have found to be effective. They are phenol, o-cresol, m-cresol, 3-ethyl phenol, 4-ethyl phenol, o-sec. butyl phenol, 2-tert. butyl phenol, 2,4-dimethyl phenol, 3,5-dimethyl phenol, 2-isopropyl phenol, butyl amine, triethyl amine, cyclohexyl amine,

TABLE 3

Effective Extractive Distillation Agents For Separating Isopropanol From 2-Butanone

| Compounds | Relative Volatility |
|---|---|
| None | 1.35 |
| Phenol | 1.55 |
| o-Cresol | 1.7 |
| m-Cresol | 2.1 |
| 3-Ethyl phenol | 1.6 |
| o-sec. Butyl phenol | 1.75 |
| 2-tert. Butyl phenol | 1.55 |
| 2,4-Dimethyl phenol | 1.5 |
| 2-Isopropyl phenol | 2.4 |
| 4-Ethyl phenol | 3.3 |

TABLE 3-continued

Effective Extractive Distillation Agents For
Separating Isopropanol From 2-Butanone

| Compounds | Relative Volatility |
| --- | --- |
| 3,5-Dimethyl phenol | 1.6 |
| Butyl amine | 2.0 |
| Triethyl amine | 1.6 |
| Cyclohexyl amine | 1.6 |
| Dimethylsulfoxide | 1.5* |
| Dimethylacetamide | 1.7* |
| 2-Nitrotoluene | 1.6 |
| Ethylene carbonate | 1.65 |
| Nitrobenzene | 1.7 |
| Ethyl acetoacetate | 1.5 |
| Methyl acetoacetate | 1.5 |
| Isobutyl isobutyrate | 1.5* |
| 2-Hydroxy acetophenone | 1.55 |
| Ethylene glycol | 2.2* |
| 1,2-Propanediol | 1.6* |
| 1,3-Butanediol | 1.75* |
| 5-Methyl-2-hexanone | 1.5 |
| 2,4-Pentanedione | 1.55 |
| Propiophenone | 1.6 |
| 1,4-Butanediol | 1.8* |
| 2-Methyl-1,3-propanediol | 1.55* |
| 1,5-Pentanediol | 1.6* |
| 1,6-Hexanediol | 1.55* |
| Glycerine | 1.6* |
| Nitromethane | 2.5 |
| Nitroethane | 2.3** |
| 1-Nitropropane | 2.4 |
| 2-Nitropropane | 2.3 |
| Butyronitrile | 1.75 |

*Brings 2-Butanone out as overhead product
**Data determined in multiplate rectification column dimethylsulfoxide, dimethylacetamide, 2-nitrotoluene, nitrobenzene, ethyl acetoacetate, methyl acetoacetate, isobutyl isobutyrate, 2-hydroxy acetophenone, ethylene glycol, 1,2-propanediol, 1,3-butanediol, 1,4-butanediol, 5-methyl-2-hexanone, 2,4-pentanedione, propiophenone, 2-methyl-1,3-propanediol, 1,5-pentanediol, 1,6-hexanediol, glycerine, nitromethane, nitroethane, 1-nitropropane, 2-nitropropane, butyronitrile and ethylene carbonate. Isomers or homologs that might be expected to be effective but which are not are p-cresol, 3-nitrotoluene and propyl butyrate.

THE USEFULNESS OF THE INVENTION

The usefulness or utility of this invention can be demonstrated by referring to the data presented in Tables 1, 2 and 3. All of the successful agents show that isopropanol can be separated from 2-butanone by means of extractive distillation in a rectification column and that the ease of separation as measured by relative volatility is considerable.

WORKING EXAMPLES

1. Fifteen grams of isopropanol, 20 grams of 2-butanone and 30 grams of o-cresol were charged to a vapor-liquid equilibrium still and refluxed for four hours. Analysis indicated a vapor composition of 47.6% isopropanol, 52.4% 2-butanone; a liquid composition of 34.7% isopropanol, 65.3% 2-butanone. This is a relative volatility of 1.7.

2. Fifteen grams of isopropanol, 20 grams of 2-butanone and 30 grams of ethylene glycol were charged to a vapor-liquid equilibrium still and refluxed for 13 hours. Analysis indicated a vapor composition of 58% isopropanol, 42% 2-butanone; a liquid composition of 75.2% isopropanol, 24.8% 2-butanone. This is a relative volatility of 2-butanone to isopropanol of 2.2.

Example 3

A solution comprising 50 grams of isopropanol and 150 grams of 2-butanone was placed in the stillpot of a 5.6 theoretical plate glass perforated plate rectification column. When refluxing began, an extractive agent comprising nitroethane was pumped into the top of the column at a rate of 15 ml/min. The temperature of the extractive agent as it entered the column was 75° C. After establishing the feed rate of the extractive agent, the heat input to the isopropanol-2-butanone in the stillpot was adjusted to give a total reflux rate of 40 ml/min. After one hour of operation, overhead and bottoms samples were collected and analysed. The overhead composition was 94.9% isopropanol, 5.1% 2-butanone and the bottoms composition was 15.2% isopropanol, 84.8% 2-butanone. This gives a relative volatility of isopropanol to 2-butanone of 2.3 for each theoretical plate.

I claim:

1. A method for recovering isopropanol from a mixture of isopropanol and 2-butanone which comprises distilling a mixture of isopropanol and 2-butanone in the presence of about one part by weight of an extractive agent per part of isopropanol—2-butanone mixture, recovering the isopropanol as overhead product and obtaining the 2-butanone and the extractive agent as bottoms product, wherein said extractive agent consists of one material selected from the group consisting of butyliamine, triethyl amine, cyclohexyl amine, 2-nitrotoluene, nitrobenzene, ethyl acetoacetate, methyl acetoacetate, 2-hydroxy acetophenone, 5-methyl-2-hexanone, 2,4-pentanedione, propiophenone, nitromethane, nitroethane, 1-nitropropane, 2-nitropropane, butyronitrile and ethylene carbonate.

2. A method for recovering 2-butanone from a mixture of 2-butanone and isopropanol which comprises distilling a mixture of 2-butanone and isopropanol in the presence of about one part by weight of an extractive agent per part of 2-butanone-isopropanol mixture, recovering the 2-butanone as overhead product and obtaining the isopropanol and the extractive agent as bottoms product, wherein said extractive agent consists of one material selected from the group consisting of dimethylsulfoxide, dimethylacetamide, glycerine, isobutyl isobutyrate, ethylene glycol, 1,2-propanediol, 1,3-butanediol, 1,4-butanediol, 2-methyl-1,3-propanediol, 1,5-pentanediol and 1,6-hexanediol.

\* \* \* \* \*